July 19, 1949. H. ROCKHILL Plant Pat. 854
STRAWBERRY PLANT
Filed July 30, 1947
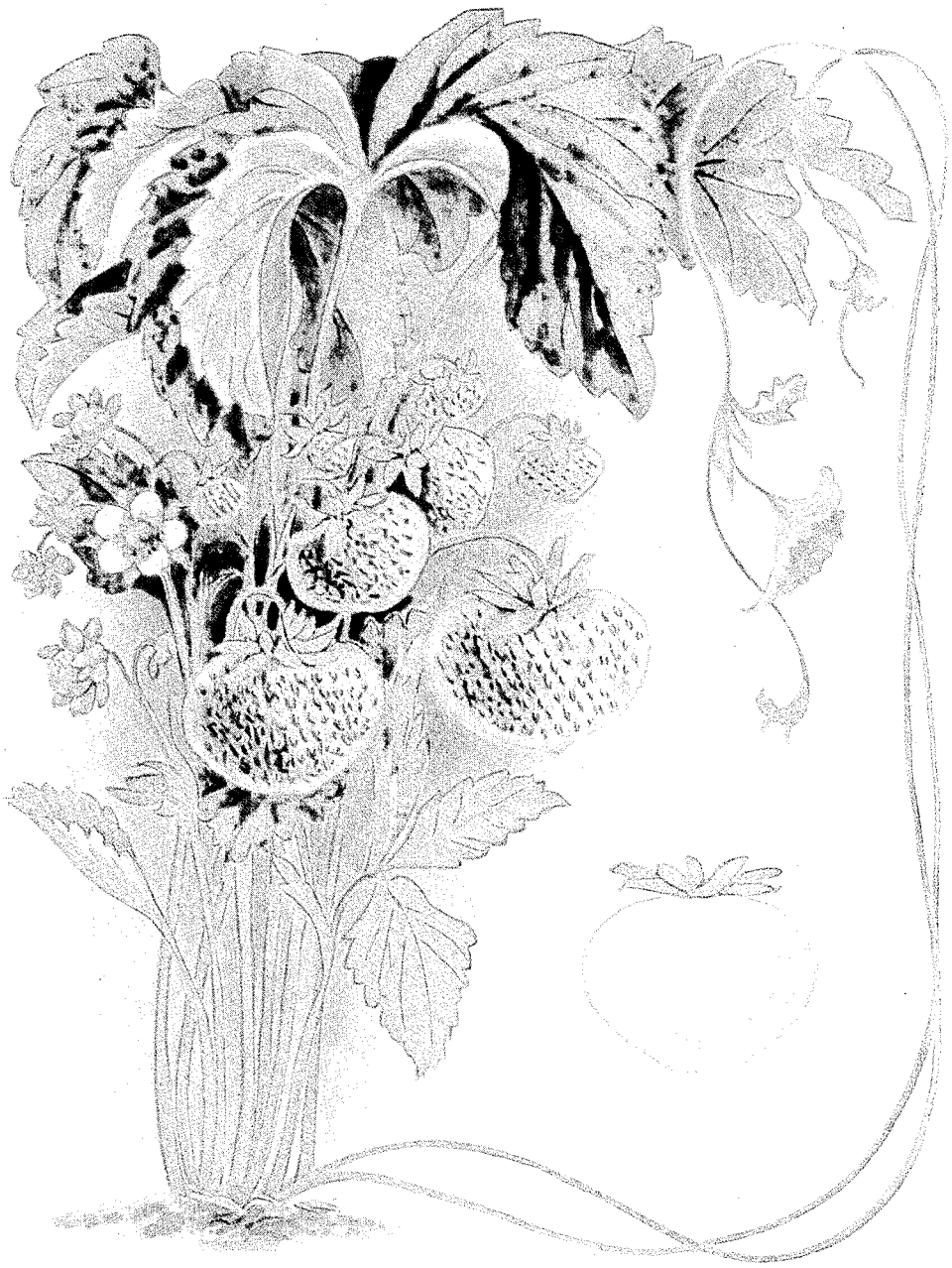
WITNESS
Addison E. Avery
HARLOW ROCKHILL, DECEASED,
by ROBERT A. ROCKHILL, EXECUTOR,
by Rummler Rummler & Snow
ATTYS.

Patented July 19, 1949

Plant Pat. 854

UNITED STATES PATENT OFFICE

854

STRAWBERRY PLANT

Harlow Rockhill, deceased, late of Conrad, Iowa, by Robert A. Rockhill, executor and trustee, Marshalltown, Iowa Application July 30, 1947, Serial No. 764,832

1 Claim. (Cl. 47—62)

The new variety of strawberry plant, herein described and illustrated, is a mutant of the well-known strawberry plant "Rockhill's Everbearing" sometimes called "Wayzata." Asexual propagation has been carried on through many generations by runners and the plant has come back true to the original mutant; thereby perpetuating the novel characteristics in the progeny.

The strawberries of this new variety are a shade lighter in color than the parent, the plants are taller and have a more profuse growth. They also make more plants which are spaced farther apart on the runner strings.

This new variety is characterized as to novelty in numerous respects, among which the following are predominantly significant:

The shiny, deep, rich red color develops uniformly over the exterior surface and is carried all through the fruit.

Ripening overall at the same time. There are no white tips to mar the beauty of a box of these berries.

The caps adhere to the berries in picking, but are easily removed.

There is no core such as is found in so many other varieties.

The berry is large, irregular round conic to short wedge, medium firm and of excellent quality.

Its exceptional sweetness suggests the flavor of a wild strawberry and it has a distinctive enticing aroma.

It has dark blue-green, healthy foliage, of heavy texture, resistant to leaf spot.

It is a vigorous grower and makes runners freely.

It can be grown to the north limits of successful strawberry culture and is adapted to heavier soils than many other varieties.

This new variety in plant structure is similar to the common strawberry. The leaves are palmately three-foliolate and toothed, all growing from the crown. The white flowers are in corymbose racemes on heavy, erect fruit stems. The calyx is deeply 5-lobed and reinforced by 3 sepal-like bracts.

The plant is exceptionally hardy and has heavy erect fruit stems which hold the fruit up off the ground. This characteristic has proved invaluable in seasons of considerable rain during the ripening period. Cleaner berries are the rule. The blossoms are perfect so that another pollenizer variety is not necessary, and the blossoms possess great frost resistance. It ripens in June, the first picking comes a few days before "Dunlap" and extends through the "Dunlap" season. It is a prolific producer of runners and progeny. There are from 6 to 16 berries per fruit stem, and the berries average 1½x1¼ inches in size.

One of its outstanding characteristics is its habit of ripening evenly all over with its rich red color extending through the entire berry. There is no pithy core and little tendency to develop central hollow cavities.

The accompanying painting shows a characteristic plant in full color, with the runners turned back upon themselves within the limits of the sheet and a single berry is also shown in section.

The color designations according to "A Dictionary of Color," by Maerz and Paul, are as follows:

| Item | Plate | Letter | Number |
|---|---|---|---|
| External surface of berry (uniform all over) | 5 | L | 5 |
| Inside flesh of berry (cross section) | 2 | J | 11 |
| Skin section (epicarp) | 3 | L | 10 |
| Leaf, upper surface | 22 | L | 8 |
| Leaf, underside | 20 | J | 5 |
| Green berries | 12 | L | 1 |

Tests indicate that this new variety of strawberry is very suitable fruit for quick freezing and locker storage.

The size, hardiness, sweetness, mid-season ripening period, adaptation to heavy soil and cooler climate, evenly distributed red coloring throughout the berry, good keeping qualities, resistance to disease, wide spacing of shoots on the runner strings, combine to make it a worthwhile commercial product.

Having thus disclosed the invention, it is claimed:

A new and distinct variety of strawberry plant, as herein shown and described, characterized as to novelty particularly by its prolific production of berries in an early mid-season fruiting period; its wild strawberry flavor; the uniform ripening of its berries; their lack of cores; the even distribution of the deep red coloring throughout the fruit; the strong upright fruit stems; and its resistance to leaf spot.

ROBERT A. ROCKHILL,

*Executor and Trustee of Harlow Rockhill, Deceased.*

No references cited.